(12) United States Patent  
Shimada

(10) Patent No.: US 10,060,852 B2  
(45) Date of Patent: Aug. 28, 2018

(54) MULTILAYER CERAMIC ELECTRONIC COMPONENT

(71) Applicant: Murata Manufacturing Co., Ltd., Nagaokakyo-shi, Kyoto-fu (JP)

(72) Inventor: Kohei Shimada, Nagaokakyo (JP)

(73) Assignee: Murata Manufacturing Co., Ltd., Kyoto (JP)

( * ) Notice: Subject to any disclaimer, the term of this patent is extended or adjusted under 35 U.S.C. 154(b) by 86 days.

(21) Appl. No.: 14/851,323

(22) Filed: Sep. 11, 2015

(65) Prior Publication Data

US 2016/0003737 A1 Jan. 7, 2016

Related U.S. Application Data

(63) Continuation of application No. PCT/JP2013/082797, filed on Dec. 6, 2013.

(30) Foreign Application Priority Data

Mar. 19, 2013 (JP) .................................. 2013-056668

(51) Int. Cl.
*H01G 4/30* (2006.01)
*G01N 21/64* (2006.01)
(Continued)

(52) U.S. Cl.
CPC ......... *G01N 21/64* (2013.01); *G01N 21/8422* (2013.01); *H01C 1/04* (2013.01); *H01G 2/24* (2013.01); *H01G 4/012* (2013.01); *H01G 4/1209* (2013.01); *H01G 4/224* (2013.01); *H01G 4/236* (2013.01); *H01G 4/30* (2013.01); *G01N 2021/8438* (2013.01); *G01N 2201/061* (2013.01); *H01G 4/12* (2013.01)

(58) Field of Classification Search
CPC ............ H01G 4/30; H01G 4/005; H01G 4/12; H01G 4/35; H01G 4/228; H01G 4/012; H01G 4/232; H01G 2/12; H01G 2/24; H05K 1/03; H05K 1/18

See application file for complete search history.

(56) References Cited

U.S. PATENT DOCUMENTS 9,754,722 B2 * 9/2017 Yamada ................... H01G 4/30
2006/0158824 A1 * 7/2006 Kawajiri ............. H01F 17/0013
361/272

(Continued)

FOREIGN PATENT DOCUMENTS

JP 60-143619 A 7/1985
JP 61-217317 A 9/1986
(Continued)

OTHER PUBLICATIONS

Official Communication issued in International Patent Application No. PCT/JP2013/082797, dated Jan. 14, 2014.

*Primary Examiner* — Nguyen Ha

(74) *Attorney, Agent, or Firm* — Keating & Bennett, LLP

(57) ABSTRACT

A multilayer ceramic capacitor includes a laminated body including laminated ceramic layers, and first and second internal electrodes extending along interfaces between the ceramic layers. External electrodes are located on outer surfaces of the laminated body. Phosphor is disposed on portions of outer surfaces of the laminated body containing no external electrodes.

19 Claims, 2 Drawing Sheets

(51) Int. Cl.
    *H01C 1/04*     (2006.01)
    *H01G 2/24*     (2006.01)
    *H01G 4/224*     (2006.01)
    *H01G 4/012*     (2006.01)
    *G01N 21/84*     (2006.01)
    *H01G 4/236*     (2006.01)
    *H01G 4/12*     (2006.01)

(56) References Cited

U.S. PATENT DOCUMENTS

| | | | | |
|---|---|---|---|---|
| 2006/0249811 | A1* | 11/2006 | Sakashita | B82Y 30/00 |
| | | | | 257/532 |
| 2009/0134956 | A1* | 5/2009 | Hadano | H01F 17/0013 |
| | | | | 333/185 |
| 2012/0261617 | A1* | 10/2012 | Pan | C09K 11/602 |
| | | | | 252/301.6 R |
| 2014/0083755 | A1* | 3/2014 | Lee | H05K 1/181 |
| | | | | 174/260 |

FOREIGN PATENT DOCUMENTS

| | | |
|---|---|---|
| JP | 63-059301 U | 4/1988 |
| JP | 11-135301 A | 5/1999 |

\* cited by examiner

MULTILAYER CERAMIC ELECTRONIC COMPONENT

BACKGROUND OF THE INVENTION

1. Field of the Invention

The present invention relates to a multilayer ceramic electronic component, and more particularly, for example, a multilayer ceramic electronic component including a laminated body that includes a plurality of ceramic layers and a plurality of internal electrodes laminated, and external electrodes on an outer surface of the laminated body.

2. Description of the Related Art

Chip-type electronic components such as capacitor chips and resistance chips are housed in tape-like packing materials. The packing materials include tapes for housing, which have a thickness. The tapes for housing have a plurality of through holes distributed in a longer direction. A cover sheet is bonded to one side of the tape for housing, chip-type electronic components are housed in the through holes of the tape for housing, and a cover sheet is bonded to the other side of the tape for housing. In this way, chip-type electronic components are obtained which are housed in tape-like packing materials (see Japanese Patent Application Laid-Open No. 61-217317).

In the case of mounting the chip-type electronic component housed in the tape-like packing material onto a circuit board, one of the cover sheets is detached. Then, the side surface of the chip-type electronic component, which is exposed from the tape for housing, is suctioned with a suction-transfer device, and the chip-type electronic component taken out from the packing material is placed on the circuit board. In this regard, with the side surface of the chip-type electronic component upward, which is suctioned with the suction-transfer device, the chip-type electronic component is mounted on the circuit board.

In this regard, when the chip-type electronic component is a multilayer ceramic electronic component that uses a laminated body including ceramic layers and internal electrodes laminated, such as a multilayer ceramic capacitor, differences will be produced in capacitance between the internal electrodes and external conductor components, magnetic field produced by the internal electrodes, etc., a magnetic field between the internal electrodes when opposed surfaces of the internal electrodes are parallel to the mounting surface of the circuit board and perpendicular thereto. Therefore, the electrical characteristics of the multilayer ceramic electronic component differ and vary depending on the relationship between the opposed orientation of the internal electrodes of the multilayer ceramic electronic component and the mounting surface of the circuit board.

In addition, even in the case of multilayer ceramic electronic components in which a plurality of internal electrodes is not opposed, such as multilayer ceramic inductors, when internal electrodes are disposed in a laminated body, electrical characteristics vary problematically depending on the disposed orientation of the internal electrodes. Thus, in order to mount the multilayer ceramic electronic component onto a circuit board so as to align the disposed orientation of the internal electrodes in the component, packing is required to align the disposed orientation of the internal electrodes.

However, in completed multilayer ceramic electronic components, internal electrodes disposed within laminated bodies are covered with ceramic layers and external electrodes, and the orientation of the internal electrodes are not able to be confirmed. In particular, when the end surfaces of the laminated bodies including the external electrode are close to square in shape, the side surfaces of the laminated bodies all have substantially the same shape, and the disposed orientation of the internal electrodes are thus not able to be determined from the shapes of the laminated bodies.

SUMMARY OF THE INVENTION

Therefore, preferred embodiments of the present invention provide a multilayer ceramic electronic component in which the disposed orientation of internal electrodes is able to be easily determined.

According to a preferred embodiment of the present invention, a multilayer ceramic electronic component includes a laminated body including a plurality of ceramic layers laminated, and internal electrodes extending along interfaces between the ceramic layers; and an external electrode located on an outer surface of the laminated body, wherein a phosphor is disposed on a portion of an outer surface of the laminated body that does not include the external electrode.

With the phosphor disposed on the portion of the outer surface of the laminated body, the phosphor produces luminescence when the phosphor is irradiated with ultraviolet rays or the like. Accordingly, when the multilayer ceramic electronic component is irradiated with ultraviolet rays or the like to capture an image with a camera, the surface of the laminated body with the phosphor provided thereon is able to be determined by image determination, and the orientation of the internal electrodes, which have a specific relationship with the position of the phosphor, is able to be determined.

In this multilayer ceramic electronic component, the phosphor preferably contains an oxide, an oxynitride, or a nitride.

In addition, the ceramic layers preferably are dielectric ceramic layers.

In addition, the phosphor preferably contains a perovskite-type compound.

This phosphor containing a perovskite-type compound preferably contains, as its main constituent, a perovskite-type compound represented by $ABO_3$, and contains R as an additive component, A contains at least one of Ba, Sr, and Ca, B contains at least one of Ti, Zr, Hf, Al, and Sn, O represents oxygen, and R can contain at least one of Ce, Pr, Nd, Sm, Eu, Gd, Tb, Dy, Ho, Er, Tm, Yb, and Y.

In addition, the internal electrodes may preferably contain a non-precious metal.

Furthermore, the external electrode may preferably contain a non-precious metal.

According to various preferred embodiments of the present invention, the outer surface of the laminated body with the phosphor located thereon is able to be easily determined by irradiating the multilayer ceramic electronic component with ultraviolet rays or the like to capture an image, and performing an image analysis. Thus, the orientation of the internal electrodes is easily known by the phosphor disposed so as to have a specific relationship with orientations of the internal electrodes. Therefore, in consideration of the orientations of the internal electrodes, the multilayer ceramic electronic component is able to be mounted onto a circuit board, and stable electrical characteristics are achieved. In addition, when the multilayer ceramic electronic component is a multilayer ceramic capacitor, vibrations of the circuit board due to the electrostrictive effect of the dielectric ceramic are significantly reduced or prevented by adjusting the orientation of the internal electrodes with respect to the mounting surface of the circuit board.

Accordingly, a sound-generating phenomenon referred to as so-called acoustic noise is significantly reduced or prevented. Furthermore, when the multilayer ceramic electronic component is a multilayer ceramic inductor, the direction of magnetic flux generation by the internal electrodes is able to be determined, and the influence of the magnetic field on the other components, etc. is reliably prevented.

The above and other elements, features, steps, characteristics and advantages of the present invention will become more apparent from the following detailed description of the preferred embodiments with reference to the attached drawings.

DETAILED DESCRIPTION OF THE PREFERRED EMBODIMENTS

Figure 1:
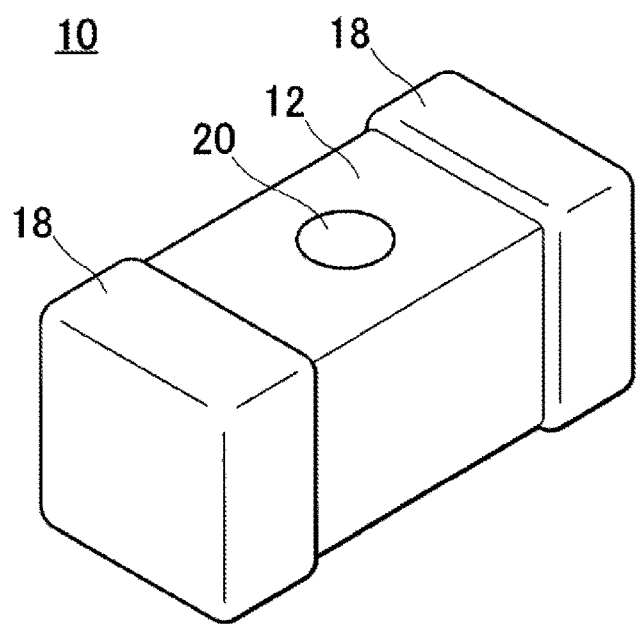
FIG. 1 is a perspective view illustrating a multilayer ceramic capacitor as an example of a multilayer ceramic electronic component according to a preferred embodiment of the present invention.

FIG. 1 is a perspective view illustrating a multilayer ceramic capacitor as an example of a multilayer ceramic electronic component according to a preferred embodiment of the present invention. The multilayer ceramic capacitor 10 includes a laminated body 12 that is preferably cuboid shaped, for example. The laminated body 12 has a length direction, a width direction, and a thickness direction. In this case, the laminated body 12 is used which has the same length in the width direction and the length direction or a ratio close to 1:1 in length.

Figure 2:
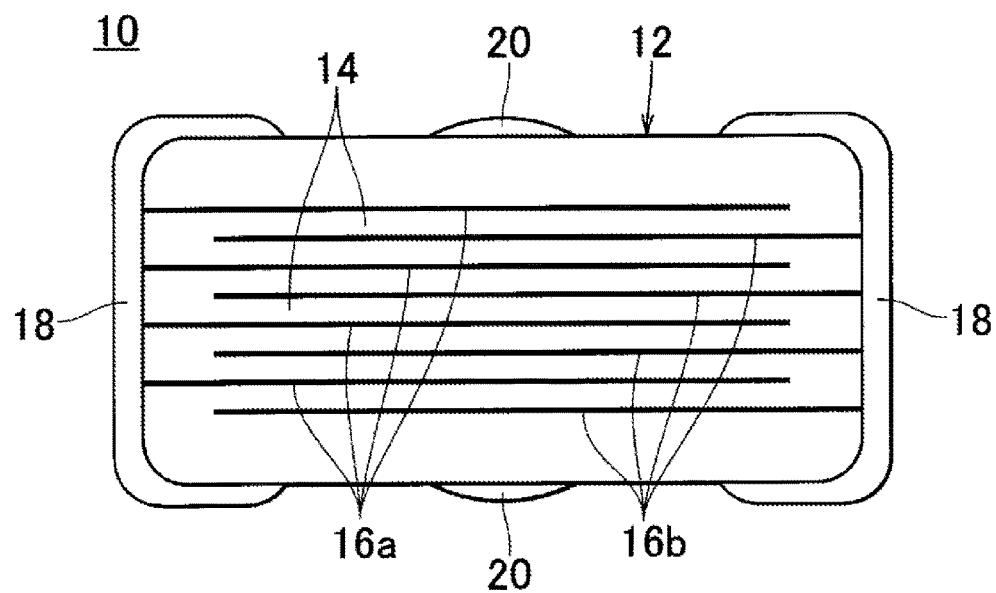
FIG. 2 is a drawing illustrating the internal structure of the multilayer ceramic capacitor shown in FIG. 1.

The laminated body 12 includes a plurality of dielectric ceramic layers 14 laminated as shown in FIG. 2. The dielectric is preferably a perovskite-type compound. Within the laminated body 12, first internal electrodes 16a and second internal electrodes 16b are provided at the interfaces of the dielectric ceramic layers 14 laminated. The first internal electrodes 16a are exposed at one end in the length direction of the dielectric ceramic layers 14, and extend from one end toward the other end, but not exposed at the other end in the length direction of the dielectric ceramic layers 14. The second internal electrodes 16b are exposed at the other end in the length direction of the dielectric ceramic layers 14, and extend from the other end toward one end, but are not exposed at one end in the length direction of the dielectric ceramic layers 14. Non-precious metals such as, for example, Ni can be used as the first internal electrodes 16a and the second internal electrodes 16b.

The laminated body 12 is structured such that the first internal electrodes 16a and the second internal electrodes 16b are alternately laminated with the dielectric ceramic layers 14 interposed therebetween, and if necessary, dielectric ceramic layers with no internal electrodes provided thereon are laminated on both sides of the laminate. Accordingly, the first internal electrodes 16a and the second internal electrodes 16b are laminated in the thickness direction of the laminated body 12 in a way that the first internal electrodes 16a and the second internal electrodes 16b are opposed to each other. Then, the first internal electrodes 16a are exposed at one end surface at one end in the length direction of the laminated body 12, whereas the second internal electrodes 16b are exposed at the other end surface at the other end in the length direction of the laminated body 12.

External electrodes 18 are provided on both ends in the length direction of the laminated body 12. Non-precious metals such as, for example, Cu can be used as the external electrodes 18. The external electrodes 18 wrap around toward the four side surfaces from the both end surfaces in the length direction of the laminated body 12. The first internal electrodes 16a and second internal electrodes 16b exposed at the both end surfaces in the length direction of the laminated body 12 are connected to the external electrodes 18. Accordingly, the first internal electrodes 16a and the second internal electrodes 16b are opposed between the two external electrodes 18, and electrostatic capacitance is generated between the two external electrodes 18.

Figure 3:
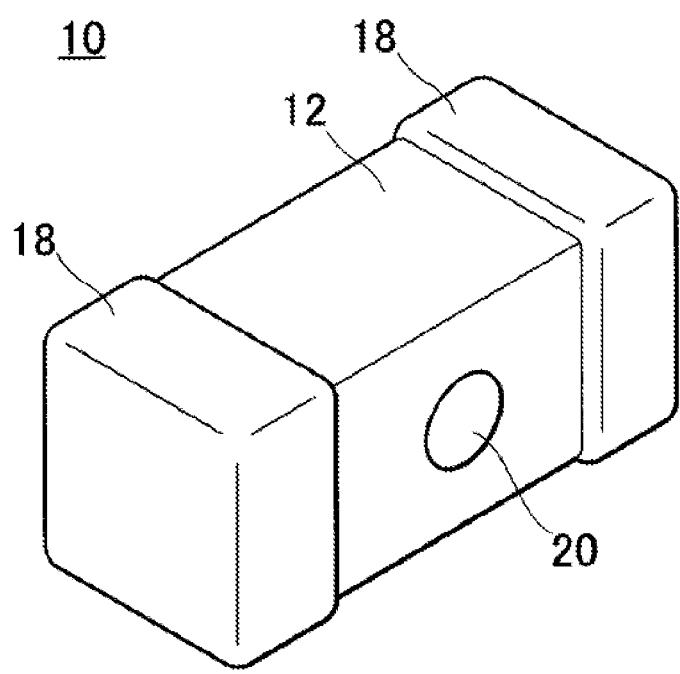
FIG. 3 is a perspective view illustrating another example of the multilayer ceramic capacitor as an example of the multilayer ceramic electronic component according to a preferred embodiment of the present invention.

On both sides in the laminating direction of the first internal electrodes 16a and second internal electrodes 16b, a phosphor 20 is disposed on the surfaces of the laminated body 12 between the two external electrodes 18. The phosphor 20 is preferably formed, for example, in the shape of a circle in central portions of the surfaces of the laminated body 12. As for the shape of the phosphor 20, the phosphor may be formed in another shape such as a rectangle or a star, for example. In addition, on the both sides in the laminating direction of the first internal electrodes 16a and second internal electrodes 16b, the phosphor 20 may be disposed over the entire surfaces of the laminated body 12 between the two external electrodes 18. Moreover, the phosphor 20 may be disposed on the side surfaces of the laminated body 12 in a direction perpendicular or substantially perpendicular to the laminating direction of the first internal electrodes 16a and second internal electrodes 16b as shown in FIG. 3.

It is to be noted that materials containing an oxide, an oxynitride, or a nitride can be used as the phosphor material. Such phosphors include $Y_2O_3$:Mn, $Ga_2O_3$:Cr, $CaGa_2O_4$:Mn, $Y_2GeO_5$:Mn, $Zn_2SiO_4$:Mn, $ZnGa_2O_4$:Mn, $Zn_2Si_{0.6}Ge_{0.4}O_4$:Mn, $Zn(Ga_{0.7}Al_{0.3})O_4$:Mn, $((Y_2O_3)_{0.6}$—$(GeO_2)_{0.4})$:Mn, $((Ga_2O_3)_{0.7}$—$(Al_2O_3)_{0.3})$:Mn, $CaAlSiN_3$:Eu, $Sr_3Si_{13}Al_3O_2N_{21}$:Eu, α-SiAlON:Eu, and β-SiAlON:Eu.

In addition, phosphors containing, as its main constituent, a perovskite-type compound represented by $ABO_3$, and containing R as an additive component can be used where A contains at least one of Ba, Sr, and Ca, B contains at least one of Ti, Zr, Hf, Al, and Sn, O represents oxygen, and R contains at least one of Ce, Pr, Nd, Sm, Eu, Gd, Tb, Dy, Ho, Er, Tm, Yb, and Y. These phosphors can be provided to the surface of the laminated body in such a way that starting materials for the phosphors are provided to an unfired laminated body with a perovskite-type compound such as barium titanate as a dielectric material, and the phosphors is synthesized by co-firing when the laminated body is subjected to firing. These phosphors include $CaTiO_3$:Pr, $Sr(Ti_{0.85}Al_{0.20})O_3$:Pr, $BaTiO_3$:Pr, $SrHfO_3$:Tm, and $CaSnO_3$:Tb.

In order to prepare this multilayer ceramic capacitor 10, a dielectric ceramic raw material is prepared. This dielectric ceramic raw material can be, with the addition of a binder, a plasticizer, an organic solvent, etc. thereto, subjected to wet mixing with a ball mill to obtain ceramic slurry. This ceramic slurry is subjected to sheet forming by, for example, a lip method to form rectangular or substantially rectangular ceramic green sheets. Onto the obtained ceramic green sheets, a conductive paste containing Ni or the like is applied by screen printing, thus forming conductive paste films to define and function as internal electrodes.

By laminating the ceramic green sheets with the conductive paste films formed thereon, and laminating, on both sides of the laminate, the ceramic green sheets with no conductive paste films formed thereon, a mother laminated body is provided. In this regard, the ceramic green sheets are laminated so that the laminated conductive paste films are exposed alternately at both end surfaces in the length direction when the mother laminated body is cut in predetermined positions. On the surface of the mother laminated body, a phosphor material is provided. In this regard, the phosphor material is disposed in central portions of side surfaces of cut raw laminated body chips when the mother laminated body is cut in predetermined positions. Alternatively, the phosphor material may be provided over the entire surface of the mother laminated body. As a method for providing the phosphor material, for example, the phosphor material in paste form may be applied to the mother laminated body, or the phosphor material in the form of a sheet may be laminated on the surface of the mother laminated body, and subjected to pressure bonding.

Then, the mother laminated body is cut in predetermined positions to obtain raw laminated body chips. With the conductive paste films formed on the ceramic green sheets as described above, the laminated conductive paste films are alternately exposed at the both end surfaces in the length direction of the raw laminated body chips. In addition, on both sides in the laminating direction of the conductive paste films, the phosphor material is provided on side surfaces of the cut raw laminated body chips.

The obtained raw laminated body chip can be heated in a $N_2$ atmosphere to burn the binder, and further subjected to firing in a reducing atmosphere with an oxygen partial pressure of about $10^{-9}$ MPa to about $10^{-12}$ MPa, thus providing the laminated body 12 including the dielectric ceramic layers 14, the first internal electrodes 16a, the second internal electrodes 16b, and the phosphor 20. A Cu paste containing glass frit is applied to both end surfaces in the length direction of the laminated body 12 obtained, and baked in a $N_2$ atmosphere to form the external electrodes 18 electrically connected to the first and second internal electrodes 16a, 16b. If necessary or desirable, the external electrodes 18 are subjected to plating. The adoption of the foregoing method is a non-limiting example of a method of preparing the multilayer ceramic capacitor 10 according to a preferred embodiment of the present invention.

In the case of the multilayer ceramic capacitor 10, the phosphor 20 produces luminescence when the multilayer ceramic capacitor 10 is irradiated with ultraviolet rays or the like, because the phosphor 20 is disposed on the side surfaces of the laminated body 12 in the laminating direction of the first and second internal electrodes 16a, 16b. Accordingly, whether the surface contains the phosphor 20 disposed or not can be determined by irradiating the multilayer ceramic capacitor 10 with ultraviolet rays or the like to capture an image with a camera, and performing image determination. Therefore, the orientation of the internal electrodes 16a, 16b is able to be aligned in housing the multilayer ceramic capacitor 10 in a tape-like packing material. Accordingly, the orientation of the first and second internal electrodes 16a, 16b with respect to a mounting surface of a circuit board is able to be aligned in mounting the multilayer ceramic capacitor 10 onto the circuit board or the like.

Thus, characteristics of the multilayer ceramic capacitor 10 mounted on the circuit board are able to be made uniform.

In addition, when an alternating-current voltage is applied to the multilayer ceramic capacitor 10, the laminated body 12 may vibrate due to the electrostrictive effect of the dielectric ceramic layers 14, and this vibration may propagate to the circuit board to vibrate the circuit board, thus generating noise referred to as so-called acoustic noise. In this case, it is assumed that mounting the multilayer ceramic capacitor 10 so that the laminating direction of the first and second internal electrodes 16a, 16b is perpendicular or substantially perpendicular to the mounting surface of the circuit board, that is, the surfaces of the first and second internal electrodes 16a, 16b are parallel or substantially parallel to the mounting surface of the circuit board will make vibrations generated in the multilayer ceramic capacitor 10 unlikely to propagate to the board, as compared with a case of mounting the multilayer ceramic capacitor 10 so that the surfaces of the first and second internal electrodes 16a, 16b are perpendicular or substantially perpendicular to the mounting surface of the circuit board. Therefore, the influence of vibrations of the multilayer ceramic capacitor 10 is reduced by mounting the multilayer ceramic capacitor 10 so that the surfaces of the first and second internal electrodes 16a, 16b are parallel or substantially parallel to the mounting surface of the circuit board. In the multilayer ceramic capacitor 10 according to a preferred embodiment of the present invention, the laminating direction of the first and second internal electrodes 16a, 16b is able to be easily known, and the multilayer ceramic capacitor 10 is thus able to be mounted onto a circuit board so that the laminating direction of the internal electrodes 16a, 16b is perpendicular or substantially perpendicular to the mounting surface of the circuit board. Thus, the influence of vibrations of the multilayer ceramic capacitor 10 is significantly reduced or prevented.

In addition, when the multilayer ceramic electronic component is a multilayer ceramic inductor or the like, the direction of magnetic flux generation is determined by the orientation of the internal electrodes, while the influence of the magnetic field on other components is significantly reduced or prevented by mounting the multilayer ceramic inductor onto a circuit board in consideration of the foregoing direction of magnetic flux generation. Therefore, also in the case of multilayer ceramic electronic components other than multilayer ceramic capacitors, advantageous effects are achieved by disposing a phosphor on side surfaces of laminated bodies to determine the orientation of internal electrodes.

It is to be noted that the phosphor 20 may be disposed on the both side surfaces of the laminated body 12 in the laminating direction of the first and second internal electrodes 16a, 16b, or may be disposed on only one of the side surfaces. Alternatively, the phosphor 20 may be disposed on the side surfaces of the laminated body 12 in a direction perpendicular or substantially perpendicular to the laminating direction of the first and second internal electrodes 16a, 16b. Also in this case, the phosphor 20 may be disposed on the both side surfaces of the laminated body 12, or the phosphor 20 may be disposed on only one of the side surfaces. When the phosphor 20 is disposed on the side surfaces of the laminated body 12 in the direction perpendicular or substantially perpendicular to the laminating direction of the first and second internal electrodes 16a, 16b, the mother laminated body is cut, and a phosphor material is then provided on the cut surfaces of the raw laminated body chip obtained.

Furthermore, after the raw laminated body chip is subjected to firing, a phosphor material may be applied on side surfaces of the sintered laminated body, and subjected to baking treatment and drying treatment. In this case, the orientation of the internal electrodes 16a, 16b is able to be known by the first internal electrodes 16a or second internal electrodes 16b exposed at ends in the length direction of the laminated body. Accordingly, a phosphor material is able to be provided on correct side surfaces of the sintered laminated body.

Example 1

The above-described example method for manufacturing a multilayer ceramic capacitor was used to prepare a multilayer ceramic capacitor. Barium titanate was used as a ceramic raw material. As starting raw materials, a $BaCO_3$ powder and a $TiO_2$ powder were weighed in predetermined amounts, subjected to wet mixing with a ball mill, dried, and then subjected to heat treatment at 1150° C. Thus, a barium titanate was obtained which was 0.15 µm in average particle size and 1.0070 in molar ratio of Ba/Ti. In the preparation of ceramic slurry, a polyvinyl butyral-based binder was used as a binder added to the ceramic raw material, and ethanol was used as an organic solvent. In addition, in the preparation of ceramic green sheets, ceramic green sheets of 4.5 µm in thickness were prepared. Internal electrodes were formed by applying a conductive paste containing Ni as its main constituent onto the ceramic green sheets.

Furthermore, in firing raw laminated body chips, the raw laminated body chips were heated at a temperature of 350° C. for 3 hours in a $N_2$ atmosphere to burn the binder.

Thereafter, a sintered laminated body was obtained by firing at 1200° C. for 2 hours in a reducing atmosphere composed of a $H_2$—$N_2$—$H_2O$ gas with an oxygen partial pressure of $10^{-10}$ MPa. It is to be noted that the Zr content in the dielectric material was increased just by a minute amount on the order of 0.02 part by mol through incorporation from YSZ balls used for mixing the materials.

The implementation of XRD structure analysis on the surface of a piece of the laminated body obtained has demonstrated that the phosphor disposed on the surface of the laminated body is a compound that has a desired structure.

Further, a Cu paste containing glass frit was applied onto both end surfaces of the sintered laminated body, and baked at a temperature of 800° C. in a $N_2$ atmosphere to form external electrodes. In this way, prepared was a multilayer ceramic capacitor with external dimensions of 1.25 mm in width, 2.0 mm in length, and 1.25 mm in thickness, where the dielectric ceramic layer interposed between the internal electrodes was 3.0 µm in thickness, the total number of effective dielectric ceramic layers was 10, and the opposed electrode area was 1.6 $mm^2$ per layer.

Table 1 shows the type of the phosphor used in this example, and the series of the phosphor. The additive amount of the luminescent center in Table 1 indicates the content of the luminescent center element with respect to 1 part by mol of the mother body of the phosphor.

For Examples 1 to 14 shown in Table 1, a phosphor paste containing a synthesized phosphor was applied to one surface of the unfired mother laminated body, and the body was cut, and then subjected to firing. For example, in the case of Example 3, 1 part by mol of $CaCO_3$ powder, 1 part by mol of $Ga_2O_3$ powder, and 0.5 part by mol of $MnCO_3$ powder are weighed as starting raw materials for the phosphor, and subjected to wet mixing with a ball mill. The powders are subjected to heat treatment at 1400° C. to synthesize a phosphor. To the phosphor material obtained in this way, a polyvinyl butyral-based binder and ethanol as an organic solvent were added to prepare a phosphor paste. For Examples 1, 2, and 4 to 14, phosphors were synthesized to prepare phosphor pastes in the same way.

In addition, for Examples 15 to 19, a phosphor starting raw material paste containing starting raw materials for the phosphor was applied to one surface of the mother laminated body, and the laminated body was cut, and then subjected to firing while the phosphor was synthesized. For example, in the case of Example 15, 1 part by mol of $CaCO_3$ powder, 1 part by mol of $TiO_2$ powder, and 0.001 part by mol of $Pr_2O_3$ powder are weighed as starting raw materials for the phosphor, and subjected to wet mixing with a ball mill. After drying the powders, a polyvinyl butyral-based binder and ethanol as an organic solvent were added thereto to prepare a phosphor starting raw material paste. Also for Examples 16 to 19, phosphor starting raw material pastes were prepared in the same way, and the laminated bodies were subjected to firing while the phosphors were synthesized.

Furthermore, a multilayer ceramic capacitor with no phosphor formed was prepared as Comparative Example 1.

TABLE 1

| | Presence or Absence of Phosphor on Laminated Body Surface | Phosphor | | | |
|---|---|---|---|---|---|
| | | | Luminescent Center | | |
| | | Mother Body of Phosphor | Element | Additive Amount (mol %) | Series of Phosphor |
| Example 1 | Presence | $Y_2O_3$ | Mn | 0.500 | Binary Oxide |
| Example 2 | Presence | $Ga_2O_3$ | Cr | 0.500 | Binary Oxide |
| Example 3 | Presence | $CaGa_2O_4$ | Mn | 0.500 | Ternary Oxide |
| Example 4 | Presence | $Y_2GeO_5$ | Mn | 0.500 | Ternary Oxide |
| Example 5 | Presence | $Zn_2SiO_4$ | Mn | 0.500 | Ternary Oxide |
| Example 6 | Presence | $ZnGa_2O_4$ | Mn | 0.500 | Ternary Oxide |
| Example 7 | Presence | $Zn_2Si_{0.6}Ge_{0.4}O_4$ | Mn | 0.500 | Multi-elemental Oxide |
| Example 8 | Presence | $Zn(Ga_{0.7}Al_{0.3})O_4$ | Mn | 0.500 | Multi-elemental Oxide |
| Example 9 | Presence | $((Y_2O_3)_{0.6}$—$(GeO_2)_{0.4})$ | Mn | 0.500 | Multi-elemental Oxide |
| Example 10 | Presence | $((Ga_2O_3)_{0.7}$—$(Al_2O_3)_{0.3})$ | Mn | 0.500 | Multi-elemental Oxide |
| Example 11 | Presence | $CaAlSiN_3$ | Eu | 0.050 | Nitride |
| Example 12 | Presence | $Sr_3Si_{13}Al_3O_2N_{21}$ | Eu | 1.600 | Oxynitride |
| Example 13 | Presence | α-SiAlON | Eu | 2.000 | Oxynitride |
| Example 14 | Presence | β-SiAlON | Eu | 2.000 | Oxynitride |
| Example 15 | Presence | $CaTiO_3$ | Pr | 0.002 | Perovskite Oxide |
| Example 16 | Presence | $Sr(Ti_{0.85}Al_{0.20})O_3$ | Pr | 0.002 | Perovskite Oxide |
| Example 17 | Presence | $BaTiO_3$ | Pr | 0.002 | Perovskite Oxide |
| Example 18 | Presence | $SrHfO_3$ | Tm | 0.050 | Perovskite Oxide |

TABLE 1-continued

| | Presence or Absence of Phosphor on Laminated Body Surface | Phosphor | | | |
| --- | --- | --- | --- | --- | --- |
| | | Mother Body of Phosphor | Luminescent Center | | Series of Phosphor |
| | | | Element | Additive Amount (mol %) | |
| Example 19 | Presence | CaSnO$_3$ | Tb | 0.050 | Perovskite Oxide |
| Comparative Example 1 | Absence | — | — | — | — |

For each sample according to the examples and comparative examples, 100 of multilayer ceramic capacitors were subjected to image determination in the case of ultraviolet irradiation to determine the laminating directions. As a result, the laminating directions of the internal electrodes in all of the multilayer ceramic capacitors were successfully figured out for the multilayer ceramic capacitors according to Examples 1 to 19, although the laminating direction of the internal electrodes was not able to be recognized for the multilayer ceramic capacitor according to Comparative Example 1.

The technique of confirming the orientation of the internal electrodes by disposing the phosphor on the side surfaces of the laminated body can be applied to all of multilayer ceramic electronic components While preferred embodiments of the present invention have been described above, it is to be understood that variations and modifications will be apparent to those skilled in the art without departing from the scope and spirit of the present invention. The scope of the present invention, therefore, is to be determined solely by the following claims.

What is claimed is:

1. A multilayer ceramic electronic component comprising:
   a laminated body including a plurality of ceramic layers laminated, and internal electrodes extending along interfaces between the plurality of ceramic layers; and
   an external electrode on an outer surface of the laminated body; wherein
   a phosphor is disposed on a portion of an outer surface of the laminated body on which the external electrode is not located; and
   the phosphor projects from the outer surface of the laminated body.

2. The multilayer ceramic electronic component according to claim 1, wherein the phosphor comprises at least one of an oxide, an oxynitride, and a nitride.

3. The multilayer ceramic electronic component according to claim 1, wherein the plurality of ceramic layers are dielectric ceramic layers.

4. The multilayer ceramic electronic component according to claim 1, wherein the phosphor comprises a perovskite-type compound.

5. The multilayer ceramic electronic component according to claim 4, wherein the phosphor contains, as a main constituent, a perovskite-type compound represented by ABO$_3$, and contains R as an additive component, A contains at least one of Ba, Sr, and Ca, B contains at least one of Ti, Zr, Hf, Al, and Sn, and O represents oxygen; and
   R contains at least one of Ce, Pr, Nd, Sm, Eu, Gd, Tb, Dy, Ho, Er, Tm, Yb, and Y.

6. The multilayer ceramic electronic component according to claim 4, wherein the internal electrodes contain a non-precious metal.

7. The multilayer ceramic electronic component according to claim 4, wherein the external electrode contains a non-precious metal.

8. The multilayer ceramic electronic component according to claim 1, wherein the multilayer ceramic electronic component is a multilayer ceramic electronic capacitor.

9. The multilayer ceramic electronic component according to claim 1, wherein the external electrode wraps around four side surfaces from both end surfaces in a length direction of the laminated body.

10. The multilayer ceramic electronic component according to claim 1, wherein the phosphor has a shape of one of a circle, a rectangle and a star.

11. The multilayer ceramic electronic component according to claim 1, wherein the external electrode is a first external electrode, a second external electrode is provided on the outer surface of the laminated body, and on both sides in a laminating direction of the internal electrodes, the phosphor is provided on entire surfaces of the laminated body between the first external electrode and the second external electrode.

12. The multilayer ceramic electronic component according to claim 1, wherein the phosphor is provided on side surfaces of the laminated body in a direction perpendicular or substantially perpendicular to a laminating direction of the internal electrodes.

13. The multilayer ceramic electronic component according to claim 1, wherein the phosphor includes at least one of Y$_2$O$_3$:Mn, Ga$_2$O$_3$:Cr, CaGa$_2$O$_4$:Mn, Y$_2$GeO$_5$:Mn, Zn$_2$SiO$_4$:Mn, ZnGa$_2$O$_4$:Mn, Zn$_2$Si$_{0.6}$Ge$_{0.4}$O$_4$:Mn, Zn(Ga$_{0.7}$Al$_{0.3}$)O$_4$:Mn, P$_2$O$_3$)$_{0.6}$—(GeO$_2$)$_{0.4}$):Mn, ((Ga$_2$O$_3$)$_{0.7}$—(Al$_2$O$_3$)$_{0.3}$):Mn, CaAlSiN$_3$:Eu, Sr$_3$Si$_{13}$Al$_3$O$_2$N$_{21}$:Eu, α-SiAlON:Eu, and β-SiAlON:Eu.

14. A method of determining an orientation of an electronic component, the method comprising the steps of:
   providing the multilayer ceramic electronic component according to claim 1;
   irradiating a surface of the multilayer ceramic electronic component with light from a light source;
   determining whether the surface of the multilayer ceramic electronic component irradiated with light from the light source contains the phosphor; and
   determining an orientation of the internal electrodes based on a result of the step of determining whether the surface of the multilayer ceramic electronic component irradiated with light from the light source contains the phosphor.

15. The method according to claim 14, further comprising the step of aligning the multilayer ceramic electronic component with respect to a mounting surface based on a result of the step of determining the orientation of the internal electrodes.

16. The method according to claim 14, further comprising the step of aligning and mounting the multilayer ceramic electronic component on a circuit board based on a result of the step of determining the orientation of the internal electrodes.

17. The method according to claim 14, wherein the light from the light source includes ultraviolet rays.

18. The method according to claim 14, wherein the phosphor is disposed on side surfaces of the laminated body in a laminating direction of the internal electrodes.

19. The multilayer ceramic electronic component according to claim 1, wherein the phosphor covers only a portion of the outer surface of the laminated body on which the external electrode is not located.

* * * * *